United States Patent
Yang et al.

(10) Patent No.: US 10,919,023 B2
(45) Date of Patent: *Feb. 16, 2021

(54) PRODUCING BDO VIA HYDROFORMYLATION OF ALLYL ALCOHOL MADE FROM GLYCERIN

(71) Applicant: Lyondell Chemical Technology, L.P., Houston, TX (US)

(72) Inventors: Xueyong Yang, Bellaire, TX (US); Daniel F. White, Houston, TX (US); Beaven S. Mandimutsira, Sugar Land, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/284,756

(22) Filed: Feb. 25, 2019

(65) Prior Publication Data

US 2019/0263737 A1 Aug. 29, 2019

Related U.S. Application Data

(60) Provisional application No. 62/635,339, filed on Feb. 26, 2018, provisional application No. 62/635,364, filed on Feb. 26, 2018.

(51) Int. Cl.

| | | |
|---|---|---|
| C07C 45/50 | (2006.01) | |
| C07C 29/60 | (2006.01) | |
| B01J 23/00 | (2006.01) | |
| B01J 31/00 | (2006.01) | |
| B01J 23/36 | (2006.01) | |
| B01J 31/22 | (2006.01) | |
| C07C 29/141 | (2006.01) | |
| C07C 31/20 | (2006.01) | |
| B01J 31/40 | (2006.01) | |
| C07C 29/143 | (2006.01) | |
| C07C 33/03 | (2006.01) | |
| C07C 47/19 | (2006.01) | |

(52) U.S. Cl.
CPC .......... B01J 23/36 (2013.01); B01J 31/2208 (2013.01); B01J 31/4046 (2013.01); C07C 29/141 (2013.01); C07C 29/143 (2013.01); C07C 29/60 (2013.01); C07C 31/207 (2013.01); C07C 45/50 (2013.01); *B01J 2231/321* (2013.01); *B01J 2531/74* (2013.01); *B01J 2531/822* (2013.01); *C07C 33/03* (2013.01); *C07C 47/19* (2013.01)

(58) Field of Classification Search
CPC ....... C07C 45/50; C07C 29/60; C07C 29/141; B01J 23/36; B01J 31/2208
See application file for complete search history.

(56) References Cited

U.S. PATENT DOCUMENTS

| | | |
|---|---|---|
| 4,064,145 A | 12/1977 | Taylor |
| 4,215,077 A | 7/1980 | Matsumoto et al. |
| 4,238,419 A | 12/1980 | Matsumoto et al. |
| 4,567,305 A | 1/1986 | Matsumoto et al. |
| 4,678,857 A | 7/1987 | Dureanleau et al. |
| 5,290,743 A | 3/1994 | Chang |
| 5,504,261 A | 4/1996 | Mullin et al. |
| 6,969,780 B1 | 11/2005 | Dubner et al. |
| 7,271,295 B1 | 9/2007 | White et al. |
| 7,279,606 B1 | 10/2007 | White |
| 7,294,602 B1 | 11/2007 | White |
| 7,612,241 B1 | 11/2009 | White et al. |
| 7,655,821 B1 | 2/2010 | White et al. |
| 7,790,932 B1 | 9/2010 | White et al. |
| 8,779,211 B2 | 7/2014 | Mandimutsira et al. |
| 8,791,305 B2 | 7/2014 | Arlt |

(Continued)

FOREIGN PATENT DOCUMENTS

| | | |
|---|---|---|
| EP | 3124462 A1 | 2/2017 |
| WO | 2013181255 A1 | 12/2013 |

OTHER PUBLICATIONS

The International Search Report and Written Opinion for PCT/US2019/019415 dated Apr. 17, 2019.

Shiramizu and Toste; Deoxygenation of Biomass-Derived Feedstocks: Oxorhenium-Catalyzed Deoxydehydration of Sugars and Sugar Alcohols, Angew. Chem. Int. Ed. 2012, vol. 51, pp. 8082-8086.

Arceo, Marsden, Bergman, and Ellman; An Efficient Didehydroxylation Method for the Biomass-Derived Polyols Glycerol and Erythritol. Mechanistic Studies of a Formic Acid-Mediated Deoxygenation; Chemical Communications, 2009, 23, pp. 3357-3359.

(Continued)

*Primary Examiner* — Sikarl A Witherspoon (57) ABSTRACT

A method including hydroformylating, with syngas, allyl alcohol in an allyl alcohol feed, to produce a hydroformylation product comprising 4-hydroxybutyraldehyde and 3-hydroxy-2-methylpropionaldehyde; and producing a 1,4-butanediol (BDO) product comprising BDO and 1,3-methylpropanediol via hydrogenation of at least a portion of the hydroformylation product. A method including hydroformylating, with syngas, allyl alcohol in a feed comprising bio-allyl alcohol, to produce a hydroformylation product comprising 4-hydroxybutyraldehyde and 3-hydroxy-2-methylpropionaldehyde; and producing a BDO product comprising BDO and 1,3-methylpropanediol via hydrogenation of at least a portion of the hydroformylation product. A method including hydroformylating, with syngas, bio-allyl alcohol in a feed comprising bio-allyl alcohol, to produce a hydroformylation product comprising 4-hydroxybutyraldehyde and 3-hydroxy-2-methylpropionaldehyde; producing a BDO product comprising BDO and 1,3-methylpropanediol via hydrogenation of at least a portion of the hydroformylation product; and removing a byproduct of the production of the bio-allyl alcohol prior to hydroformylating the bio-allyl alcohol and/or from the BDO-product.

20 Claims, 1 Drawing Sheet

(56) References Cited

U.S. PATENT DOCUMENTS

2010/0292514 A1    11/2010    White

OTHER PUBLICATIONS

Valentino Canale et al; Deoxydehydration of Glycerol to Allyl Alcohol Catalyzed by Rhenium Derivatives, Catalysis Science & Technology, vol. 4, No. 10, Jun. 20, 2014, pp. 3697-3704, XP55243388, United Kingdom, ISSN 2044-4753, DOI 10.1039/C4CY00631C.
Jing Yi et al; Rhenium-Catalyzed Transfer Hudrogenation and Deoxygenation of Biomass-Derived Polyols to Small and Useful Organics, Chemsuschem, vol. 5, No. 8, Aug. 12, 2012, pp. 1401-1404, XP55086116, ISSN 1864-5631, DOI 10.1002/cssc.201200138.

PRODUCING BDO VIA HYDROFORMYLATION OF ALLYL ALCOHOL MADE FROM GLYCERIN

CROSS-REFERENCE TO RELATED APPLICATIONS

This application claims the benefit of priority to U.S. Provisional Patent Application Nos. 62/635,339 and 62/635,364, each filed on Feb. 26, 2018, which are incorporated herein by reference in their entirety.

TECHNICAL FIELD

This disclosure relates to the production of 1,4-butanediol (BDO). More specifically, this disclosure relates to the production of BDO from allyl alcohol. Still more specifically, this disclosure relates to the production of BDO from allyl alcohol made from glycerin.

BACKGROUND 1,4-butanediol (BDO) is produced commercially from allyl alcohol (see, for example, U.S. Pat. No. 4,215,077). A need exists for improved methods for the production of BDO, and according to the present disclosure such improved methods may utilize allyl alcohol derived from glycerin and/or bio-glycerin, thereby providing a novel for the excess bio-glycerin produced in the production of bio-diesel.

SUMMARY

Herein disclosed is a method comprising: hydroformylating, with synthesis gas, allyl alcohol in a feed comprising allyl alcohol derived from glycerin, to produce a hydroformylation product comprising 4-hydroxybutyraldehyde (HBA) and 3-hydroxy-2-methylpropionaldehyde (HMPA); and producing a 1,4-butanediol (BDO) product comprising BDO and 1,3-methylpropanediol (MPD) via hydrogenation of at least a portion of the hydroformylation product.

Also disclosed herein is a method comprising: hydroformylating, with synthesis gas, allyl alcohol in a feed comprising bio-allyl alcohol derived from bio-glycerin, to produce a hydroformylation product comprising 4-hydroxybutyraldehyde (HBA) and 3-hydroxy-2-methylpropionaldehyde (HMPA); and producing a 1,4-butanediol (BDO) product comprising BDO and 1,3-methylpropanediol (MPD) via hydrogenation of at least a portion of the hydroformylation product.

Also disclosed herein is a method comprising: hydroformylating, with synthesis gas, bio-allyl alcohol in a feed comprising bio-allyl alcohol derived from bio-glycerin, to produce a hydroformylation product comprising 4-hydroxybutyraldehyde (HBA) and 3-hydroxy-2-methylpropionaldehyde (HMPA); producing a 1,4-butanediol (BDO) product comprising BDO and 1,3-methylpropanediol (MPD) via hydrogenation of at least a portion of the hydroformylation product; and removing a byproduct of the production of the bio-allyl alcohol prior to hydroformylating the bio-allyl alcohol, from the BDO-product, or both.

BRIEF DESCRIPTION OF THE DRAWING

The following figures illustrate embodiments of the subject matter disclosed herein. The claimed subject matter may be understood by reference to the following description taken in conjunction with the accompanying figures, in which:

DETAILED DESCRIPTION

Overview

This disclosure relates to the production of 1,4-butanediol (BDO) from allyl alcohol made from glycerin.

Production of BDO (and/or MPD) from Allyl Alcohol

Figure 1:
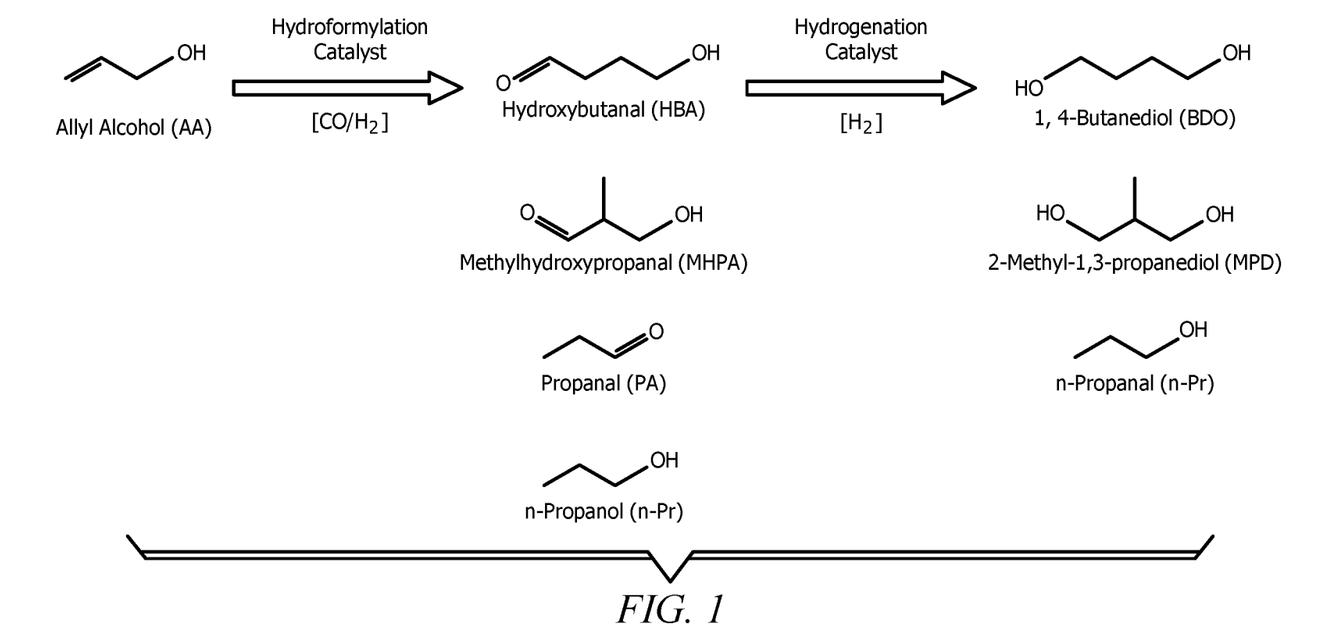
FIG. 1 is a schematic of the conversion of allyl alcohol (AA) to 1,4-butanediol (BDO) according to embodiments of this disclosure.

Allyl alcohol may be utilized for the production of 1,4-butanediol (BDO), which occurs via the chemical pathway depicted in FIG. 1. As indicated in FIG. 1, in the hydroformylation reaction, allyl alcohol (AA) is reacted with a CO/H2 gas mixture (also referred to herein as 'synthesis gas' or 'syngas') in the presence of a hydroformylation catalyst to form 4-hydroxybutyraldehyde (HBA; also known as hydroxybutanal). The HBA may then be separated from the catalyst, e.g., by water extraction, and hydrogenated to form 1,4-butanediol (BDO). One disadvantage of the hydroformylation process is that other co-products or byproducts are also formed in addition to the desired HBA linear product. The hydroformylation of allyl alcohol typically produces some 3-hydroxy-2-methylpropionaldehyde (HMPA; also known as methylhydroxypropanal (MHPA)), which is a branched co-product, and C3 byproducts, such as, without limitation, n-propanol (NPA, n-Pr) and propionaldehyde (propanal; PA). Although HMPA may be hydrogenated to produce 1,3-methyl propanediol (MPD), which is a useful material, the MPD co-product reduces the yield of BDO. Formation of the byproducts effectively represents another yield loss in the process, which can adversely affect the process economics.

Hydroformylation of Allyl Alcohol to HBA (and HMPA)

According to this disclosure, at least a portion of the allyl alcohol from which the BDO is produced is derived from glycerin. The allyl alcohol can be subjected to hydroformylation by contact with a hydroformylation catalyst. Hydroformylation methods and catalyst are described, for example, in U.S. Pat. Nos. 4,064,145; 4,215,077; 4,238,419; 4,567,305; 4,678,857; 5,290,743; 4,678,857; 7,294,602; 7,271,295; 7,279,606; 7,612,241; 7,655,821; 7,790,932; 8,791,305; and 8,779,211, the disclosure of each of which is hereby incorporated herein by reference in its entirety for purposes not contrary to this disclosure.

As noted above, various catalyst systems have been employed for the hydroformylation reaction. Some such hydroformylation catalysts and processes employ a rhodium complex together with a phosphine ligand. In embodiments, the process of this disclosure comprises hydroformylating allyl alcohol in the presence of a solvent and a hydroformylation catalyst system. In embodiments, the hydroformylation catalyst system comprises a rhodium complex and a phosphine ligand. Such phosphine ligands include trisubstituted phosphines such as triphenyl phosphine, a monophosphine ligand. In embodiments, the phosphine ligand can comprise one or more selected from diphosphine ligands, monophosphines, and combinations thereof. In embodiments, at least a portion of the allyl alcohol derived from glycerin (e.g., via the hereinbelow-noted rhenium catalyst) is hydroformylated via a hydroformylation catalyst as disclosed in U.S. Pat. Nos. 7,294,602; 7,271,295; 7,279,606; 7,612,241, 7,655,821; 7,790,932; and/or 8,779,211, In embodiments, the hydroformylation catalyst system comprises a rhodium complex and a diphosphine ligand, such as trans-1,2-bis(bis(3,5-di-n-alkylphenyl) phosphinomethyl)cyclobutane, as described, for example, in U.S. Pat. Nos. 7,294,602 and 7,279,606. In embodiments, the diphosphine ligand comprises trans-1,2-bis(bis(3,5-dimethylphenyl) phosphinomethyl) cyclobutane (also known as trans-1, 2-bis[di(3,5-dimethylphenyl) phosphinomethyl] cyclobutane). Trans-1,2-bis(bis(3,5-di-n-alkyl-phenyl)phosphinomethyl)cyclobutane has the chemical structure:

wherein R is an n-alkyl group. In embodiments, R is methyl, ethyl, or propyl. In embodiments, the disphosphine ligand can be trans-1,2-bis(bis(3,5-dimethylphenyl)phosphinomethyl) cyclobutane or trans-1,2-bis(bis(3, 5-diethyl-phenyl) phosphinomethyl) cyclobutane. The trans-1,2-bis(bis(3,5-di-n-alkylphenyl) phosphinomethyl) cyclobutane may be prepared by any possible method. For instance, it may be prepared by the reaction of trans-1,2-cyclobutanedimethanol, bis(toluenesulfonate) with lithium di(3,5-di-n-alkylphenyl)phosphine. The ligands and catalyst compositions described herein are commercially available or may be made according to the methods, procedures and processes described in Smith, M., & March, J. (2007). *Marchs Advanced organic chemistry: Reactions, mechanisms, and structure*. Hoboken, N.J.: Wiley-Interscience; Regalbuto, J. R. (2007) *Handbook of catalyst preparation*. Boca Raton: Taylor & Francis; and Kamer, P. C., (2012) *Phosphorus(III) Ligands in Homogeneous Catalysis: Design and Synthesis*. Wiley.

In embodiments, the hydroformylation catalyst system further comprises a rhodium complex. Such rhodium complexes may contain rhodium attached to ligand groups. In embodiments, the rhodium complex is soluble in the solvent. There are no particular restrictions regarding the choice of ligands attached to the rhodium complex. For example, such ligands include hydrides, carbonyl, substituted and unsubstituted cyclopentadienyls, 2,4-alkanedionates, trialkyl or triaryl phosphines, diphosphines, and mixtures thereof. In embodiments, the ligands attached to the rhodium complex are selected from carbonyl, acetylacetonate (2,4-pentanedionate), triphenylphosphine, and mixtures thereof. Examples of rhodium complexes include, without limitation, (acetylacetonato)dicarbonyl rhodium(I) (also known as dicarbonyl-acetylacetonato-rhodium(I), dicarbonylrhodium (I) 2,4-pentanedionate, $Rh(CO)_2(acac)$, and rhodium(I) dicarbonyl acetylacetonate) and tris(triphenylphosphine) rhodium carbonyl hydride.

The rhodium complex can be pre-associated with the phosphine (e.g., trans-1,2-bis(bis(3,5-di-n-alkylphenyl) phosphinomethyl)cyclobutane) prior to use in the hydroformylation reaction such that the [bis(bis(3,5-di-n-alkylphenyl)-phosphinomethyl)cyclobutane] ligand forms part of the rhodium complex, or it can be added separately. However, in embodiments, the rhodium complex is added separately from the phosphine ligand (e.g., the trans-1,2-bis (bis(3,5-di-n-alkylphenyl)phosphinomethyl)cyclobutane).

In embodiments, the molar ratio of the phosphine ligand: rhodium complex (e.g., the trans-1,2-bis(bis(3,5-di-n-alkylphenyl)-phosphinomethyl) cyclobutane:rhodium complex) can be in the range of 0.5:1 to 5:1.

In embodiments, the hydroformylation catalyst system comprises a rhodium complex and one or more diphosphine ligands, the rhodium complex comprises $Rh(CO)_2(acac)$, and the molar ratio of $Rh(CO)_2(acac)$ to the diphosphine ligands is in the range of from 0.1:1 to 1:5, from 0.9:1.5 to 1:3, or from 1:1.9 to 1:2.1.

In embodiments, the hydroformylation catalyst system may additionally comprise an auxiliary ligand, such that the hydroformylation is further performed in the presence of the auxiliary ligand, which is added to the catalyst solution. In embodiments, the auxiliary ligand comprises a monophosphine.

In embodiments, the monophosphine compound is in addition to any phosphine ligand that may be associated with the rhodium complex. In embodiments, the monophosphine compound is a trisubstituted phosphine that is represented by the formula:

$$(R^1)_3P,$$

wherein $R^1$ is an alkyl or aryl group. Aliphatic $R^1$ groups may include methyl, ethyl, n-butyl, sec-butyl, octyl, and/or decyl. Aromatic $R^1$ groups may include phenyl, tolyl, and/or naphthyl. The $R^1$ groups may be the same or are different. In embodiments, the monophosphine is a trisubstituted aryl phosphine. In embodiments, the monophosphine is triphenylphosphine or tritolylphosphine. In embodiments, the monophosphine is triphenyl phosphine.

In embodiments, the hydroformylation catalyst system comprises a diphosphine ligand and a monophosphine, and the monophosphine is present such that a ratio of the diphosphine to the monophosphine is in the range of from 1:1 to 1:3, from 1:1.2 to 1:2, or from 1:1.4 to 1:1.6.

Hydroformylation may be performed in the presence of a hydroformylation reaction solvent. Typical solvents are those that are capable of solubilizing the rhodium complex and are not reactive to the hydroxyaldehydes that are produced in the hydroformylation step. Solvents may include an organic solvent having very low or minimal solubility in water. In embodiments, the hydroformylation reaction solvent is selected from C5-C20 aliphatic hydrocarbons, C6-C20 aromatic hydrocarbons, alcohols, ethers, or mixtures thereof. Without limitation, in embodiments, the hydroformylation reaction solvent is selected from toluene, cyclohexane, methyl t-butyl ether, xylenes, or mixtures thereof. In embodiments, the hydroformylation reaction solvent is dry degassed toluene.

Typical reaction conditions for the hydroformylation step are mild to favor the formation of the linear ('1') 4-hydroxybutyraldehyde (HBA) rather than branched ('b') 3-hydroxy-2-methylpropionaldehyde (HMPA) reaction product. In embodiments, hydroformylation reaction conditions comprise temperatures in the range of from 20 to 120° C., from 45 to 85° C., from 50 to 80° C., from 35° C. to 120° C., from 45° C. to 95° C., or from 50° C. to 70° C., or greater than or equal to 55° C., 60° C., or 65° C. In embodiments, hydroformylation reaction conditions comprise pressures in the range of from 20 psig to 600 psig, from 30 psig to 400 psig, from 40 psig to 300 psig, from 100 psig to 400 psig, or from 120 psig to 300 psig, or greater than or equal to 180 psig, 190 psig, or 200 psig, The molar ratio of carbon monoxide to hydrogen (CO:H2) can be about 1:1, although the ratio can vary considerably. In embodiments, the synthesis gas comprises a molar ratio of carbon monoxide to hydrogen in the range of from 0.5:1.5 to 1.5:0.5, from 0.8:1.2 to 0.9:1.1, or from 0.95:1.05 to 0.98:1.12, or greater than or equal to 1:1.

The partial pressure of CO may be within the range of 5 to 100 psig. The partial pressure of hydrogen may be within the range of 40 to 200 psig. In embodiments, the hydroformylation reaction is conducted at these conditions until a predominance of the allyl alcohol has reacted, e.g. 60 to 99.9 mole percent, and the products comprise primarily 4-hydroxybutyraldehyde (HBA) with some branched reaction products. The amount of reaction time may not be critical, however, a reaction time of from 0.5 to 4 hours may be adequate.

In embodiments, the allyl alcohol starting concentration on a hydroformylation reaction solvent to feed basis is in the range of from 5 to 40 percent by weight in the solvent; in embodiments, an allyl alcohol starting concentration on a hydroformylation reaction solvent to feed basis in the range of from 5 to 10 percent by weight may be utilized.

In embodiments, the hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference for purposes not contrary to this disclosure. In embodiments, the liquid phase hydrogen: carbon monoxide molar ratio is in the range of from 10:1 to 1:2, or from 5:1 to 1:2.

The conversion of allyl alcohol to hydroformylation product can be defined as:

$$AA \text{ Conversion}=(([AA]_{feed}-[AA]_{unreacted})/([AA]_{feed}))\times 100\%, \quad (3)$$

wherein $[AA]_{feed}$ is the molar amount of allyl alcohol in the feed to the hydroformylation reaction, and $[AA]_{unreacted}$ is the molar amount of unreacted allyl alcohol in the hydroformylation reaction product. In embodiments, the conversion of allyl alcohol to hydroformylation product is greater than or equal to 99.0, 99.1, 99.2, 99.3, 99.4, 99.5, 99.6, 99.7, or 99.8 mole percent.

In embodiments, a molar ratio of HBA to HMPA in the hydroformylation product is greater than or equal to 10:1, 10.5:1, 11:1, or 11.5:1. In embodiments, the hydroformylation product further comprises one or more byproducts selected from C3 products, including n-propanol, propionaldehyde, and combinations thereof. In embodiments, a sum total amount of the one or more byproducts (i.e., products other than HBA and HMPA) is less than or equal to 0.5, 0.4, or 0.3 mole percent.

Hydrogenation of Hydroformylation Product

In embodiments, following the hydroformylation step, the HBA product is separated from the solvent and hydroformylation catalyst system, for example via water extraction in an extraction vessel. Any water extraction methods may be used and can be effected by any means, such as mixer-settlers, packed or trayed extraction columns, rotating disk contactors, or passed to a settling tank for resolution of the mixture into aqueous and organic phases. HBA, and any HMPA, remain soluble in the water (aqueous) phase and are separated from the solvent (organic) phase.

The HBA (and/or any HMPA) in the hydroformylation product can be hydrogenated to provide BDO (and/or MPD). Thus, in embodiments, the HBA (and any HMPA) reaction product is subjected to an additional step of hydrogenating the HBA in the presence of a hydrogenation catalyst to produce BDO. The hydrogenation may be performed via any suitable method, for example, as described in U.S. Pat. Nos. 6,969,780 or 5,504,261, the disclosure of each of which is hereby incorporated herein in its entirety for purposes not contrary to this disclosure. As indicated in the schematic of FIG. 1, hydrogen can be added to the reaction vessel for the hydrogenation. Such hydrogenation catalysts include any Group VIII metal, such as nickel, cobalt, ruthenium, platinum, and palladium, as well as copper, zinc and chromium and mixtures and alloys thereof. In embodiments, the hydrogenation catalyst is selected from nickel catalysts. In embodiments, the hydrogenation catalyst is selected from RANEY®-type nickel and fixed bed nickel catalysts.

In embodiments, the hydrogenation reaction is carried out at a temperature in the range of from 60 to 200° C., from 80 to 140° C., or from 95 to 105° C. In embodiments, the hydrogenation is carried out at a pressure in the range of from 200 to 1000 psig, from 300 to 1000 psig, or from 700 to 900 psig. In embodiments, the hydrogenation is effected for a hydrogenation reaction time in the range of from 1 to 10 hours. During the hydrogenation reaction, BDO and MPD are formed. In embodiments, a high ratio of linear to branched products (i.e., BDO to MPD) is achieved, along with a low amount of any other co-product/byproducts (e.g., n-propanol). In embodiments, the molar ratio of BDO to MPD in the hydrogenation product is greater than or equal to 10:1, 10.5:1, 11:1, or 11.5:1. In embodiments, the hydrogenation further comprises one or more byproducts selected from C3 products, including n-propanol. In embodiments, a sum total amount of the one or more byproducts (i.e., products other than BDO and MPD) is less than or equal to 0.5, 0.4, or 0.3 mole percent.

Production of Allyl Alcohol from Glycerin

According to this disclosure, at least a portion of the allyl alcohol hydroformylated to produce BDO is produced or derived, from glycerin (e.g., glycerin produced or derived from any source including bio-glycerin derived from bio-fuel, e.g., bio-diesel, production and/or non-bio-glycerin derived from conventional petrochemical processes). In embodiments, at least a portion of the allyl alcohol hydroformylated, according to this disclosure, to produce BDO is produced or derived from bio-glycerin, and is thus considered herein a 'bio-allyl alcohol,' and the subsequently produced BDO can be considered a 'bio-BDO'. In embodiments, at least 20, 30, 40 50, 60, 70, 80, or 90 mole percent of the allyl alcohol converted to BDO according to this disclosure is derived from bio-glycerin. In embodiments, at least 20, 30, 40 50, 60, 70, 80, or 90 mole percent of the allyl alcohol converted to BDO according to this disclosure is derived from non-bio-glycerin.

A method of this disclosure may further comprise producing at least a portion of the allyl alcohol in the feed comprising allyl alcohol from glycerin, e.g., bio- and/or non-bio-glycerin. The allyl alcohol may be produced from glycerin via any operable method and with any operable catalyst. Preparation of allyl alcohol from glycerin may be performed according to any operable methodology such as (i) a two-step reaction mechanism, including a first step for dehydration of glycerin into acrolein and a second step for hydrogenation of acrolein into allyl alcohol, (ii) direct preparation of allyl alcohol from glycerin not through acrolein, and/or (iii) preparation of allyl alcohol from glycerin without the use of a catalyst. Challenges with various reported preparation methods of allyl alcohol include the need for an expensive (e.g., methyltrioxorhenium) catalyst, high levels of impurities (e.g., byproducts, such as octene), and/or low allyl alcohol yield. For example, the conversion of glycerin to allyl alcohol (AA) has been reported by Shiramizu and Toste 2012 (Angew. Chem. Int. Ed. 2012, Vol. 51, pp. 8082-8086); Arceo, Marsden, Bergman, and Ellman 2009 (Chemical Communications, 2009, 23, 3357); Yi, Liu, and Abu-Omar 2012 (ChemSusChem, 2012, 5, 1401).

In embodiments, at least a portion of the allyl alcohol hydroformylated according to this disclosure is produced by contacting glycerin (e.g., bio- and/or non-bio-glycerin) with an MTO catalyst, for example, as described by Toste, et al. In such embodiments, methyltrioxorhenium (MTO) may be utilized in a reaction in which an excess (10 equivalents or more) of a secondary alcohol such as 3-octanol is utilized as the reductant as well as solvent, with reactions being carried out in a closed vessel at temperatures above 170° C. In addition to 3-octanone resulting from oxidative dehydrogenation reaction, byproduct octene isomers may be formed as the result of dehydration reactions. Toste, et al. reported that, when employing MTO as catalyst and 3-octanol as solvent, glycerin could be converted to AA with a selectivity of 90%. However, for each mole of AA produced, 1.1 mole of 3-octanol was also being converted into octene isomers.

In embodiments, (at least a portion of) the allyl alcohol hydroformylated according to this disclosure is produced utilizing a formic-acid mediated conversion of glycerin (e.g., bio- and/or non-bio-glycerin) to allyl alcohol, as described, for example, by Arceo, Marsden, Bergman, and Ellman.

Figure 2:
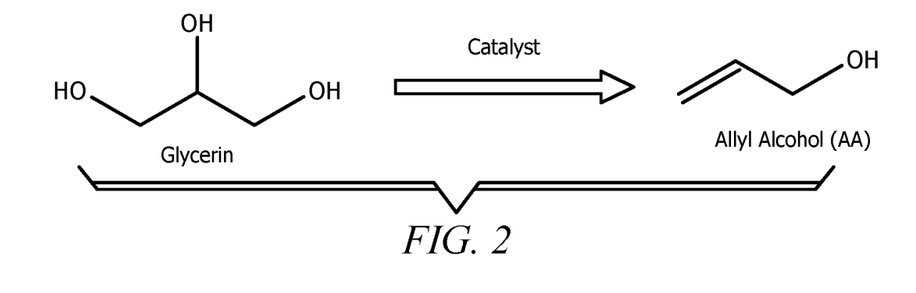
FIG. 2 is a schematic of the conversion of glycerin to allyl alcohol (AA) in the presence of a rhenium catalyst, according to embodiments of this disclosure.

In embodiments, (at least a portion of) the allyl alcohol hydroformylated according to this disclosure is produced by exposing glycerin (e.g., bio- and/or non-bio-glycerin) to a desired temperature (e.g., a temperature of greater than 140° C.) in the presence of a catalyst to produce a product comprising allyl alcohol, as depicted in FIG. 2. At least a portion or the entirety of the allyl alcohol hydroformylated according to this disclosure may be produced and/or be a product of the catalyst and method for producing allyl alcohol that is described in U.S. Patent Application No. 62/635,364, incorporated herein by reference in its entirety for purposes not contrary to this disclosure. In such embodiments, the catalyst employed comprises rhenium dioxide (also referred to as rhenium (IV) oxide or $ReO_2$) and/or rhenium trioxide (also referred to as rhenium (VI) oxide or $ReO_3$), and at least a portion of the allyl alcohol subjected to hydroformylation is produced by subjecting glycerin (e.g., bio- and/or non-bio-glycerin) to conversion conditions in the presence of the catalyst comprising rhenium trioxide, rhenium dioxide, or a combination thereof to produce a product comprising allyl alcohol.

In embodiments, the catalyst comprising rhenium dioxide and/or rhenium trioxide is present in the range of from 0.5 to 10 mole percent, from 2.5 to 7.5 mole percent, from 3 to 5 mole percent, from 4 to 5 mole percent, or from 4.5 to 5 mole percent of total moles of glycerin. In embodiments, the catalyst comprising rhenium dioxide and/or rhenium trioxide is present at a level of less than or equal to 2, 3, 4, or 5 mole percent.

Glycerin, represented by the chemical formula $HOCH_2(CHOH)CH_2OH$, is also referred to as trihydroxypropane or glycerol. Although the purity of the glycerin converted to allyl alcohol via the herein-disclosed catalyst and method does not limit the scope of this disclosure, it can be 80 wt. % or higher, 90 wt. % or higher, or 95 wt. % or higher, in embodiments, in order to reduce the production of reaction byproducts. In embodiments, the glycerin is obtained as a byproduct from the synthesis of bio-diesel via transesterification of vegetable oil and alcohol. Such glycerin may be referred to as bio-glycerin or crude glycerin, and the produced allyl alcohol may thus be considered 'bio-allyl alcohol'. As used herein, 'bio-glycerol', 'bio-glycerin', 'crude glycerin', and 'crude glycerol' refer to glycerin obtained as a byproduct of bio-diesel production, and 'bio-allyl alcohol' refers to allyl alcohol derived from bio-glycerin. In embodiments, the glycerin converted to allyl alcohol (and subsequently to BDO) via the herein disclosed method comprises bio-glycerin, and the product comprises bio-allyl alcohol; in embodiments, the glycerin converted to allyl alcohol (and subsequently BDO) via the herein disclosed method comprises non-bio-glycerin, and the product comprises non-bio-allyl alcohol; in embodiments, the glycerin converted to allyl alcohol (and subsequently BDO) via the herein disclosed method comprises bio- and non-bioglycerin, and the product comprises bio-allyl alcohol and non-bio-allyl alcohol.

The conversion of glycerin to allyl alcohol according to embodiments of this disclosure can be a liquid phase reaction, and conversion conditions can comprise a reaction temperature of greater than 140° C., 150° C., 160° C., 170° C., 180° C., 190° C., or 200° C. The reaction can be effected under ambient pressure, and the reaction temperature can be increased to the operating temperature within 30 minutes in the presence of the catalyst (e.g., $ReO_2$ and/or $ReO_3$ catalyst).

The conversion of glycerin to allyl alcohol may be effected with or without a solvent. In embodiments, the glycerin is exposed to the reaction temperature in the presence of a solvent. In embodiments, a catalyst system comprises $ReO_3$ and a solvent; in embodiments, a catalyst system comprises $ReO_2$ and a solvent; in embodiments, a catalyst system comprises $ReO_2$ and/or $ReO_3$, and a solvent. In embodiments, the solvent comprises a secondary alcohol. In embodiments, the solvent comprises 3-octanol. In embodiments comprising a solvent, an initial molar ratio of the solvent to glycerin can be in the range of from 30 to 1, from 20 to 1, from 15 to 1, from 5 to 1, from 1 to 1, or less than or equal to 15 to 1, 10 to 1, or 6 to 1.

An allyl alcohol (AA) selectivity can be defined as:

$$\text{AA Selectivity} = (([AA]_{produced})/([Glycerin]_{feed} - [Glycerin]_{unreacted})) \times 100\%, \quad (1)$$

wherein $(([AA]_{produced}$ is the molar amount of produced allyl alcohol, $[Glycerin]_{feed}$ is the molar amount of glycerin in the glycerin feed to the reaction, and $-[Glycerin]_{unreacted}$ is the molar amount of unreacted glycerin in the reaction product. The selectivity to allyl alcohol may, in embodiments, be greater than or equal to 50%, 60%, 70%, 80%, or 90%.

A glycerin conversion can be defined as:

$$\text{Glycerin Conversion} = (([Glycerin]_{feed} - [Glycerin]_{unreacted})/([Glycerin]_{feed})) \times 100\%, \quad (2)$$

wherein $[Glycerin]_{feed}$ is the molar amount of glycerin in the feed to the reaction, and $[Glycerin]_{unreacted}$ is the molar amount of unreacted glycerin in the reaction product. The glycerin conversion may, in embodiments, be greater than or equal to 50, 60, 70, 75, or 80 mole percent, or in the range of from 50 to 100 mole percent, from 60 to 100 mole percent, from 70 to 100 mole percent, from 70 to 90 mole percent, or from 80 to 90 mole percent.

The yield of allyl alcohol (defined by the glycerin conversion multiplied by the AA selectivity) may, in embodiments, be greater than or equal to 60%, 70%, 80%, 85%, or 90%.

As noted above, Toste, et al. reported that the use of methyltrioxorhenium (MTO) in a reaction in which an excess of a secondary alcohol such as 3-octanol is utilized as solvent, resulted in the production of 3-octanone resulting from oxidative dehydrogenation reaction, along with byproduct octene isomers formed as the result of dehydration reactions. For each mole of allyl alcohol produced, one mole of 3-octanol was converted into undesirable octene isomers. The formation of the octene isomers may increase the cost of making allyl alcohol using an MTO/3-octanol catalyst system, due to removal of these octene isomers from the product allyl alcohol (or further downstream).

Utilization of the above-noted rhenium catalyst and method may, in embodiments employing 3-octanol as solvent, provide for a product comprising allyl alcohol that further comprises a reduced molar amount of octene isomers relative to the same method employing a methyltrioxorhenium (MTO) catalyst. For example, in embodiments, the product comprising allyl alcohol comprises less than 1.0, 0.9, 0.8, 0.7, 0.6, 0.5, 0.4, 0.3, 0.2, 0.15, 0.11, or 0.10 mole of octene isomers per mole of allyl alcohol produced.

When employing 3-octanol as solvent, the product comprising allyl alcohol can further comprise 3-octanone as a byproduct. In such embodiments, a molar ratio of 3-octanone byproduct to allyl alcohol in the product comprising allyl alcohol can be less than or equal to 1.6:1, 1.5:1, 1.4:1, 1.3:1, 1.2:1, 1.1:1, or 1.0:1. In embodiments, 3-octanone is separated from the product comprising allyl alcohol. At least a portion of the separated 3-octanone can be hydrogenated to provide 3-octanol, which may be recycled for use as solvent/reductant. As 3-octanone can be readily converted back to 3-octanol for recycle and/or reuse, production of 3-octanone may be more desirable than production of octene isomers, which may be separated from the product comprising allyl alcohol, but utilizable primarily for fuel.

The allyl alcohol hydroformylated according to this disclosure may be produced using any operable vessel(s) or reactor(s). For example, any one or more selected from batch reactors, continuous stirred tank reactors, and plug flow reactors, which are used by those of skill in the art, may be employed, and the kind and combination thereof are not limited herein.

Features/Potential Benefits

The herein-disclosed methods enable the production of BDO from allyl alcohol derived from glycerin (bio- and/or non-bio-glycerin); in embodiments, at least a portion of the allyl alcohol from which BDO is produced according to this disclosure is derived from bio-glycerin. In embodiments, the allyl alcohol is produced by and/or is a product of the conversion of glycerin to allyl alcohol utilizing a rhenium catalyst.

The following examples merely illustrate the system and method of this disclosure. Those skilled in the art will recognize many variations that are within the spirit of this disclosure and the scope of the claims.

EXAMPLES

Example 1

Catalytic Hydroformylation of Bio-Allyl Alcohol Derived from Glycerin

A hydroformylation experiment using allyl alcohol (AA) produced from glycerin was carried out in anhydrous toluene with the stoichiometry determined by the amount of rhodium. In a typical experiment, a rhodium complex, $Rh(CO)_2(acac)$ (1 equivalent) was added to this solution of dry degassed toluene (15 g) and the diphosphine ligand, trans-1,2-bis(bis(3,5-di-n-alkylphenyl) phosphinomethyl) cyclobutane) (2 equivalent). This solution was then transferred to a 50 mL Parr autoclave. The autoclave was then flushed three times with a 1:1 $CO/H_2$ mixture, and pressurized to 180 psig, and the autoclave heated with stirring to the indicated temperature, for example 65° C. Once the desired temperature was stably attained for at least five (5) minutes, allyl alcohol solution (3.5 mL) in the presence of low level octene isomers was injected and the autoclave pressure increased to 200 psig with the $CO:H_2$ gas mixture. The reactor was then maintained at a constant 200 psig pressure and the gas uptake with time was monitored until there was no further gas uptake. The reactor was cooled and depressurized, and the resulting solution was analyzed by gas chromatography to determine the products of the reaction, including HBA, HMPA and C3 products (n-propanol and propionaldehyde). Bio-AA derived from bio-glycerin was used for Runs 1 and 2 of the hydroformylation reaction. The performance of Runs 1 and 2, along with the performance of non-bio-allyl alcohol (i.e., standard allyl alcohol purchased from SIGMA ALDRICH) is summarized in Table 1. The hydroformylation results show that bio-AA behaves substantially the same as regular (i.e., non-bio-) allyl alcohol, and impurities such as octenes did not substantially affect the hydroformylation reaction.

TABLE 1

Hydroformylation Results from Example 1

| | Bio-AA (Run 1) | Bio-AA (Run 2) | Non-Bio-AA |
|---|---|---|---|
| Conversion (mole %) | 99.8 | 99.6 | 99.3 |
| 1:b* (HBA/HMPA) | 11.7 | 11.8 | 10.5 |
| C3, Propanal, Propanol (mole %) | 0.4 | 0.4 | 0.3 |

*linear to branched

Additional Disclosure

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method comprising: hydroformylating, with synthesis gas, allyl alcohol in a feed comprising allyl alcohol derived from glycerin, to produce a hydroformylation product comprising 4-hydroxybutyraldehyde (HBA) and 3-hydroxy-2-methylpropionaldehyde (HMPA); and producing a 1,4-butanediol (BDO) product comprising BDO and 1,3-methylpropanediol (MPD) via hydrogenation of at least a portion of the hydroformylation product.

B: A method comprising: hydroformylating, with synthesis gas, allyl alcohol in a feed comprising bio-allyl alcohol derived from bio-glycerin, to produce a hydroformylation product comprising 4-hydroxybutyraldehyde (HBA) and 3-hydroxy-2-methylpropionaldehyde (HMPA); and producing a 1,4-butanediol (BDO) product comprising BDO and 1,3-methylpropanediol (MPD) via hydrogenation of at least a portion of the hydroformylation product.

C: A method comprising: hydroformylating, with synthesis gas, bio-allyl alcohol in a feed comprising bio-allyl alcohol derived from bio-glycerin, to produce a hydroformylation product comprising 4-hydroxybutyraldehyde (HBA) and 3-hydroxy-2-methylpropionaldehyde (HMPA); producing a 1,4-butanediol (BDO) product comprising BDO and 1,3-methylpropanediol (MPD) via hydrogenation of at least a portion of the hydroformylation product; and removing a byproduct of the production of the bio-allyl alcohol prior to hydroformylating the bio-allyl alcohol, from the BDO-product, or both.

Each of embodiments A, B, and C may have one or more of the following additional elements:

Element 1: wherein the feed comprises bio-allyl alcohol derived from bio-based glycerin, non-bio-allyl alcohol derived from non-bio-based glycerin, or a combination thereof. Element 2: wherein the feed comprising allyl alcohol further comprises acrolein, lactic acid, octene isomers, or a combination thereof, and wherein the method further comprises removing acrolein, lactic acid, octene isomers, or a combination thereof from the feed prior to hydroformylating the allyl alcohol, from the BDO-product, or both. Element 3: wherein hydroformylation is performed in anhydrous toluene, with a rhodium catalyst in the presence of phosphine ligands, or both. Element 4: wherein the hydroformylation is performed in the presence of a catalyst solution comprising a rhodium catalyst comprising $Rh(CO)_2(acac)$ and one or more phosphine ligands. Element 5: wherein the one or more phosphine ligands comprise a diphosphine, and wherein the molar ratio of $Rh(CO)_2(acac)$ to the diphosphine ligands is from 0.1:1 to 1:5, from 0.9:1.5 to 1:3, or from 1:1.9 to 1:2.1. Element 6: wherein the diphosphine ligand comprises trans-1,2-bis[di(3,5-dimethylphenyl)phosphinomethyl]cyclobutane. Element 7: wherein the hydroformylation is further performed in the presence of an auxiliary ligand, which is added to the catalyst solution. Element 8: wherein the auxiliary ligand comprises a monophosphine. Element 9: wherein the monophosphine is present such that a ratio of the diphosphine to the monophosphine is in the range of from 1:1 to 1:3, from 1:1.2 to 1:2, or from 1.4 to 1.6. Element 10: wherein the monophosphine comprises triphenylphosphine. Element 11: wherein the hydroformylation is carried out at a pressure in the range of from 20 psig to 600 psig, from 100 psig to 400 psig, or from 120 psig to 300 psig, or greater than or equal to 180 psig, 190 psig, or 200 psig, and a temperature in the range of from 35° C. to 120° C., from 45° C. to 95° C., or from 50° C. to 70° C., or greater than or equal to 55° C., 60° C., or 65° C. Element 12: wherein a conversion of allyl alcohol to hydroformylation product, defined as: AA Conversion=$((([AA]_{feed}-[AA]_{unreacted})/([AA]_{feed}))\times 100\%$, is greater than or equal to 99.0, 99.1, 99.2, 99.3, 99.4, 99.5, 99.6, 99.7, or 99.8 mole percent. Element 13: wherein a molar ratio of HBA to HMPA in the hydroformylation product is greater than or equal to 10, 10.5, 11, or 11.5. Element 14: wherein the hydroformylation product further comprises one or more byproducts selected from C3 products, including n-propanol, propionaldehyde, and combinations thereof, and wherein a sum total amount of the one or more byproducts is less than or equal to 0.5, 0.4, or 0.3 mole percent. Element 15: wherein the synthesis gas comprises a molar ratio of carbon monoxide to hydrogen in the range of from 0.5:1.5 to 1.5:0.5, from 0.8:1.2 to 0.9:1.1, or from 0.95:1.05 to 0.98:1.12, or greater than or equal to 1:1. Element 16: further comprising producing at least a portion of the allyl alcohol in the feed comprising allyl alcohol derived from glycerin by exposing glycerin to a temperature of greater than 140° C. in the presence of a catalyst to produce a product comprising allyl alcohol. Element 17: wherein the catalyst comprises rhenium trioxide, rhenium dioxide, methyltrioxorhenium (MTO) or a combination thereof. Element 18: wherein the glycerin is exposed to a temperature of greater than 140° C. in the presence of a solvent. Element 19: wherein the solvent comprises a secondary alcohol. Element 20: wherein the secondary alcohol comprises 3-octanol. Element 21: wherein the catalyst comprises rhenium trioxide, rhenium dioxide, or a combination thereof, and wherein the product comprising allyl alcohol comprises a reduced molar amount of octene isomers relative to the same method employing a methyltrioxorhenium (MTO) catalyst. Element 22: wherein the reduced molar amount of octene isomers comprises less than 1.0, 0.9, 0.8, 0.7, 0.6, 0.5, 0.4, 0.3, or 0.2, 0.15, 0.11, or 0.10 mole of octene isomers per mole of allyl alcohol produced. Element 23: wherein an allyl alcohol (AA) selectivity, defined as AA Selectivity=$(([AA]_{produced})/([Glycerin]_{feed}-[Glycerin]_{unreacted}))\times 100\%$, is greater than or equal to 50%, 60%, 70%, 80%, or 90%. Element 24: wherein the product comprising allyl alcohol further comprises 3-octanone byproduct. Element 25: further comprising separating 3-octanone from the product comprising allyl alcohol, and hydrogenating at least a portion of the separated 3-octanone to provide 3-octanol. Element 26: wherein a molar ratio of 3-octanone byproduct to allyl alcohol in the product comprising allyl alcohol is less than or equal to 1.6, 1.5, 1.4, 1.3, 1.2, 1.1, or 1.0. Element 27: wherein an initial molar ratio of the solvent to glycerin is in the range of from 30 to 1, from 20 to 1, from 15 to 1, from 5 to 1, from 1 to 1, or less than or equal to 6 to 1. Element 28: wherein the catalyst is present in the range of from 0.5 to 10, from 2.5 to 7.5, from 3 to 5, from 4 to 5, or from 4.5 to 5 mole percent, or less than or equal to 2, 3, 4, or 5 mole percent. Element 29: wherein a glycerin conversion, defined as: Glycerin Conversion= $(([Glycerin]_{feed}-[Glycerin]_{unreacted})/([Glycerin]_{feed}))\times 100\%$, is greater than or equal to 50, 60, 70, 75, or 80 mole percent, or in the range of from 50 to 100, 60 to 100, 70 to 100, 70 to 90, or 80 to 90 mole percent. Element 30: wherein at least a portion of the glycerin comprises bio-glycerin, wherein the product comprising allyl alcohol thus comprises bio-allyl alcohol, and wherein the product comprising bio-allyl alcohol further comprises acrolein, lactic acid, octene isomers, or a combination thereof. Element 31: further comprising removing acrolein, lactic acid, octene isomers, or a combination thereof from the product comprising allyl alcohol prior to hydroformylating the allyl alcohol, from the BDO-product, or both. Element 32: wherein the bio-glycerin is exposed to a temperature of greater than 140° C. in the presence of a solvent. Element 33: wherein the byproduct comprises acrolein, lactic acid, octene isomers, or a combination thereof. Element 34: further comprising producing at least a portion of the bio-allyl alcohol in the feed by exposing bio-glycerin to a temperature of greater than 140° C. in the presence of a catalyst to produce a product comprising bio-allyl alcohol. Element 35: wherein the bio-glycerin is exposed to a temperature of greater than 140° C. in the presence of a solvent.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method comprising:
   producing allyl alcohol from glycerin in the presence of 0.5 to 10 mole percent of a rhenium catalyst, wherein the rhenium catalyst is selected from the group consisting of rhenium dioxide, methyltrioxorhenium (MTO), rhenium trioxide and a combination thereof,
   hydroformylating, with synthesis gas, allyl alcohol in a feed comprising allyl alcohol derived from glycerin, to produce a hydroformylation product comprising 4-hydroxybutyraldehyde (HBA) and 3-hydroxy-2-methylpropionaldehyde (HMPA) in a ratio of HBA:HMPA of at least 11.5:1; and
   producing a 1,4-butanediol (BDO) product comprising BDO and 1,3-methylpropanediol (MPD) via hydrogenation of at least a portion of the hydroformylation product.

2. The method of claim 1, wherein the feed comprises bio-allyl alcohol derived from bio-based glycerin, non-bio-allyl alcohol derived from non-bio-based glycerin, or a combination thereof.

3. The method of claim 1, wherein the feed comprising allyl alcohol further comprises acrolein, lactic acid, octene isomers, or a combination thereof, and wherein the method further comprises removing acrolein, lactic acid, octene isomers, or a combination thereof from the feed prior to hydroformylating the allyl alcohol, from the BDO-product, or both.

4. The method of claim 1, wherein hydroformylation is performed in anhydrous toluene, with a rhodium catalyst in the presence of phosphine ligands, or both.

5. The method of claim 4, wherein the hydroformylation is performed in the presence of a catalyst solution comprising a rhodium catalyst comprising $Rh(CO)_2(acac)$ and one or more phosphine ligands.

6. The method of claim 5, wherein the one or more phosphine ligands comprise a diphosphine, and wherein the molar ratio of $Rh(CO)_2(acac)$ to the diphosphine ligands is from 0.1:1 to 1:5.

7. The method of claim 4, wherein the hydroformylation is carried out at a pressure in the range of from 20 psig to 600 psig, and a temperature in the range of from 35° C. to 120° C.

8. The method of claim 1, wherein the hydroformylation product further comprises one or more byproducts selected from C3 products, including n-propanol, propionaldehyde, and combinations thereof, and wherein a sum total amount of the one or more byproducts is less than or equal to 0.5 mole percent.

9. The method of claim 1, wherein the synthesis gas comprises a molar ratio of carbon monoxide to hydrogen in the range of from 0.5:1.5 to 1.5:0.5.

10. The method of claim 1 further comprising producing at least a portion of the allyl alcohol in the feed comprising allyl alcohol by exposing glycerin to a temperature of greater than 140° C. in the presence of the rhenium catalyst to produce a product comprising allyl alcohol.

11. The method of claim 10, wherein the rhenium catalyst is present in an amount ranging from 3 to 10 mole percent, and wherein the feed comprising allyl alcohol contains less than 1.0 mole percent of octene isomers per mole of allyl alcohol.

12. A method comprising:
    producing bio-allyl alcohol from bio-glycerin in the presence of 0.5 to 10 mole percent of a rhenium catalyst, wherein the rhenium catalyst is selected from the group consisting of rhenium dioxide, methyltrioxorhenium (MTO), rhenium trioxide and a combination thereof,
    hydroformylating, with synthesis gas, allyl alcohol in a feed comprising bio-allyl alcohol derived from bio-glycerin, to produce a hydroformylation product comprising 4-hydroxybutyraldehyde (HBA) and 3-hydroxy-2-methylpropionaldehyde (HMPA) in a ratio of HBA:HMPA of at least 11.5:1; and
    producing a 1,4-butanediol (BDO) product comprising BDO and 1,3-methylpropanediol (MPD) via hydrogenation of at least a portion of the hydroformylation product.

13. The method of claim 12 further comprising producing at least a portion of the bio-allyl alcohol in the feed by exposing bio-glycerin to a temperature of greater than 140° C. in the presence of a catalyst to produce a product comprising bio-allyl alcohol.

14. The method of claim 13, wherein the rhenium catalyst is present in an amount ranging from 2.5 to 7.5 mole percent, and wherein the feed comprising bio-allyl alcohol contains less than 1 mole percent of octene isomers per mole of bio-allyl alcohol.

15. The method of claim 13, wherein the bio-glycerin is exposed to a temperature of greater than 140° C. in the presence of a solvent.

16. A method comprising:
producing bio-allyl alcohol from bio-glycerin in the presence of 0.5 to 10 mole percent of a rhenium catalyst, wherein the rhenium catalyst is selected from the group consisting of rhenium dioxide, methyltrioxorhenium (MTO), rhenium trioxide and a combination thereof;
hydroformylating, with synthesis gas, bio-allyl alcohol in a feed comprising bio-allyl alcohol derived from bio-glycerin, to produce a hydroformylation product comprising 4-hydroxybutyraldehyde (HBA) and 3-hydroxy-2-methylpropionaldehyde (HMPA) in a ratio of HBA:HMPA of at least 11.5:1;
producing a 1,4-butanediol (BDO) product comprising BDO and 1,3-methylpropanediol (MPD) via hydrogenation of at least a portion of the hydroformylation product; and
removing a byproduct of the production of the bio-allyl alcohol prior to hydroformylating the bio-allyl alcohol, from the BDO-product, or both.

17. The method of claim 16, wherein the byproduct comprises acrolein, lactic acid, octene isomers, or a combination thereof.

18. The method of claim 16 further comprising producing at least a portion of the bio-allyl alcohol in the feed by exposing bio-glycerin to a temperature of greater than 140° C. in the presence of the rhenium catalyst to produce a product comprising bio-allyl alcohol.

19. The method of claim 18, wherein the rhenium catalyst is present in an amount ranging from 2.5 to 7.5 mole percent.

20. The method of claim 18, wherein the bio-glycerin is exposed to a temperature of greater than 140° C. in the presence of a solvent.

* * * * *